United States Patent [19]
Kim

[11] Patent Number: 6,110,500
[45] Date of Patent: Aug. 29, 2000

[54] COATED TABLET WITH LONG TERM PARABOLIC AND ZERO-ORDER RELEASE KINETICS

[75] Inventor: Cherng-ju Kim, North Wales, Pa.

[73] Assignee: Temple University, Philadelphia, Pa.

[21] Appl. No.: 09/047,863

[22] Filed: Mar. 25, 1998

[51] Int. Cl.[7] .............................. A61K 9/00; A61K 9/32; A61K 9/36

[52] U.S. Cl. .......................... 424/475; 424/464; 424/465; 424/468; 424/469; 424/474; 424/479; 424/480; 424/482

[58] Field of Search ................... 424/464, 465, 424/468–482

[56] References Cited

U.S. PATENT DOCUMENTS

| | | | |
|---|---|---|---|
| D. 283,649 | 4/1986 | Casberg | D28/2 |
| 2,312,381 | 3/1943 | Bickenheuser | 167/57 |
| 3,113,076 | 12/1963 | Jacobs | 167/82 |
| 3,146,169 | 8/1964 | Stephenson et al. | 167/82 |
| 3,279,995 | 10/1966 | Reid | 167/82 |
| 3,923,939 | 12/1975 | Baker et al. | 264/49 |
| 4,217,898 | 8/1980 | Theeuwes | 128/260 |
| 4,218,433 | 8/1980 | Kooichi et al. | 424/15 |
| 4,264,573 | 4/1981 | Powell et al. | 424/19 |
| 4,361,545 | 11/1982 | Powell et al. | 424/19 |
| 4,601,893 | 7/1986 | Cardinal | 424/15 |
| 4,663,147 | 5/1987 | DePrince | 424/467 |
| 4,800,083 | 1/1989 | Hom et al. | 424/457 |
| 4,816,262 | 3/1989 | McMullen | 424/467 |
| 4,994,273 | 2/1991 | Zentner | 424/422 |
| 5,004,614 | 4/1991 | Staniforth | 424/466 |
| 5,219,621 | 6/1993 | Geoghegan et al. | 424/462 |
| 5,256,440 | 10/1993 | Appel et al. | 427/3 |
| 5,336,504 | 8/1994 | Geoghegan et al. | 424/462 |
| 5,342,627 | 8/1994 | Chopra et al. | 424/473 |
| 5,376,771 | 12/1994 | Roy | 219/121.71 |
| 5,478,573 | 12/1995 | Eichel et al. | 424/480 |
| 5,489,294 | 2/1996 | McVenes et al. | 607/120 |
| 5,529,790 | 6/1996 | Eichel et al. | 424/480 |
| 5,536,507 | 7/1996 | Abramowitz et al. | 424/479 |
| 5,549,913 | 8/1996 | Colombo et al. | 424/472 |
| 5,582,838 | 12/1996 | Rork et al. | 424/472 |

FOREIGN PATENT DOCUMENTS

| | | |
|---|---|---|
| 0 259 219 A2 | 3/1988 | European Pat. Off. . |
| 0 542 364 B1 | 5/1993 | European Pat. Off. . |
| WO 94/01239 | 1/1994 | WIPO . |
| WO 96/29058 | 9/1996 | WIPO . |

OTHER PUBLICATIONS

Grant and Hach's Dictionary p. 464, 1987.

Sangali, M.E. et al., *Inert Monolithic Device with Central Hole for Constant Drug Release*, Proceedings of the Intern. Symp. Control Rel. Bioact. Mater., pp.316–320, (1993), Controlled Release Society, Inc.

(List continued on next page.)

*Primary Examiner*—Gollamudi S. Kishore
*Attorney, Agent, or Firm*—Ratner & Prestia

[57] ABSTRACT

A tablet for the controlled release of an active pharmaceutical ingredient. The tablet comprises a core having a donut-like configuration with a cylindrical hole extending through the center of the core. The core of the body comprises at least one active pharmaceutical agent and at least one hydrophilic, water-soluble, polymeric carrier. The core is coated with a hydrophobic, water-insoluble material covering all of the core except that which is defined by the cylindrical hole. Also included is a method of preparing a tablet for the controlled release of an active ingredient. The method comprises the steps of blending an active pharmaceutical ingredient, a water-soluble hydrophilic, polymeric carrier, and optionally an excipient, to form a mix; compressing the mix; punching a tablet from the mix; coating the tablet in a water insoluble, hydrophobic coating, then drilling a hole through the coated tablet. A second embodiment of this method includes drilling a first hole through the tablet before coating the tablet, placing a rod through the first hole, dipping the tablet into the coating, and then removing the rod and drilling a second hole in the tablet which is larger than the first hole.

6 Claims, 8 Drawing Sheets

OTHER PUBLICATIONS

Hansson, Arne G. et al., *Perforated Coated Tablets for Controlled Release of Drugs at a Constant Rate*, Journal of Pharmaceutical Sciences, pp. 322–324, (vol. 77, Apr. 1988), American Pharmaceutical Assoc.

Vandelli, M.A. et al., *Selective Coating of Cylindrical Matrices with a Central Hole: An Interpretation of the Swelling Process*, International Journal of Pharmaceutics, pp. 107–114, (vol. 100, 1993), Elsevier Science Publishers B.V.

Benkorah, Amal Y. et al., *Concave Coated, Centrally Perforated Tablets for Oral Controlled Drug Delivery*, Journal of Controlled Release, pp. 155–160, (Release 32, 1994), Elsevier Science B.V.

Bechard, S. et al., *Solute Release from a Porous Polymeric Matrix: Inwardly Tapered Disk with a Central Releasing Hole*, Journal of Pharmaceutical Sciences, pp. 222–228, (vol. 77, No. 3, Mar. 1998), American Pharmaceutical Assn.

Vandelli, M.A. et al., *Selective Coating of Cylindrical Matrices with a Central Hole: II, An Interpretation of the Release Process*, International Journal of Pharmaceutics, pp.115–121, (vol. 100, 1993), Elsevier Science Publishers B.V.

Rhine, William D. et al., *A New Approach to Achieve Zero–Order Release Kinetics from Diffusion–Controlled Polymer Matrix Systems*, Controlled Release of Bioactive Materials (1980), Academic Press, Inc.

Nelson, K.G. et al., *Constant–Release Diffusion Systems—Rate Controlled by Means of Geometric Configuration*, pp.324–340, (1987), American Chemical Society.

Lipper, R.A. et al., *Analysis of Theoretical Behavior of a Proposed Zero Order Drug Delivery System*, pp. 163–164, Journal of Pharmaceutical Sciences, (vol. 66, No. 2, Feb. 1977), American Pharmaceutical Association.

Kuu, Wei–Youh et al., *Multiple–Hole Approach to Zero–Order Release*, pp. 926–933, Journal of Pharmaceutical Sciences, (vol. 74, No. 9, Sep. 1985), American Pharmaceutical Association.

Boettner, W.A. et al., *The Morantel Sustained Release Trilaminate: A Device for the Controlled Ruminal Delivery of Morantel to Cattle*, pp.23–30, Journal of Controlled Release, (vol. 8, 1988), Elsevier Science Publishers.

Nangia, A. et al., *Novel Regulated Release System Based on Geometric Configuration*, Proceedings of the Intern. Symp. Control Rel. Bioact. Mater., pp.294–295, (1995), Controlled Release Society, Inc.

Bayomi, Mohsen A., *Geometric Approach for Zero–Order Release of Drugs Dispersed in an Inert Matrix*, pp. 914–916, Pharmaceutical Research, (vol. 11, No. 6, 1994), Plenum Publishing Corp.

Kim, Cherng–ju, *Compressed Donut–Shaped Tablets with Zero–Order Release Kinetics*, pp. 1045–1048, Pharmaceutical Research, (vol. 12, No. 7, 1995), Plenum Publishing Corporation.

COATED TABLET WITH LONG TERM PARABOLIC AND ZERO-ORDER RELEASE KINETICS

FIELD OF INVENTION

This invention relates generally to drug releasing tablets. More specifically, this invention relates to tablets for delivering water-soluble drugs over a long period of time at a nearly constant rate.

BACKGROUND OF THE INVENTION

A well known practice for storing, and later delivering, an active ingredient involves forming the matter into compact tablets from which the matter can later be dissociated or released. One such use involves drug delivery where the drug is administered orally (or otherwise) into an organic system. Particularly, diffusion-controlled matrix devices have received a great deal of attention for drug delivery systems in past years. One approach has been to use insoluble porous disc matrices, in which the drug is loaded into the matrix to an amount greater than its solubility limit in the dissolution medium. It has been found, however, that the rate of solute diffusion out of these tablets is not consistent over time. Often, the diffusion rate changes with the square root of time. In such cases, the amount of drug available at a biologic site of absorption decreases quickly as a function of time if the absorption rate is greater than the drug release from the matrix, as it often is with the systems of the past.

This problem is significant in view of the fact that it is often desirable to have a steady rate of drug delivery. More specifically, a parabolic or zero order release kinetic is often desirable where drug delivery is desired to be constant over a given time period.

With much of the prior art, as the dissolution occurs, the surface area (i.e. the interface), between the solvent and active agent changes with time. If this dissolution begins at the outside surface of a tablet, as dissolution progresses the surface area between the active agent and the solvent decreases. Where a coated tablet has been drilled with a hole to allow solvent and active agent to interface beginning in the area where the hole was drilled, the surface area between the solvent and the active agent increases with time and thus the rate of dissolution increases with time. These problems continue to be the focus of attempts to achieve constant, or near constant, release of active agents into an organic body over time.

Simple monolithic tablets for extended release dosages have been fabricated by compressing a mixture of a water-insoluble polymer, a drug, and excipients. Such tablets may yield first-order kinetics or square-root-of-time kinetics. An inherent limitation of this type of monolithic matrix is the increase in diffusional length resistance over time due to the insolubility of the polymer.

SUMMARY OF INVENTION

The present invention provides a tablet for the controlled release of an active ingredient. The tablet comprises a body having a donut-like configuration with a cylindrical hole extending coaxially through the center of the body. The core material of the body comprises at least one active pharmaceutical agent and at least one hydrophilic, water-soluble, polymeric carrier. The core material is coated with a hydrophobic, water-insoluble material covering all of the core material except that which is defined by the cylindrical hole.

Also included in the present invention is a method of preparing a tablet for the controlled release of an active ingredient. The method comprises the steps of mixing an active pharmaceutical ingredient, a hydrophilic, water soluble, polymeric carrier, and optionally an excipient; compressing the mix; punching a tablet from the mix; coating the tablet, and drilling a hole in the center of the tablet.

A second embodiment of the method includes the extra steps of drilling a first hole through the tablet before it is coated, coating the drilled tablet, and then drilling the tablet a second time with a hole larger than the first drilled hole. This method allows the tablet to be placed onto a rod (through the first hole), and inserted into the coating material during the coating process. The second drilling is performed to insure that the inner exposed area is clear of all coating.

BRIEF DESCRIPTION OF THE DRAWING

The invention is best understood from the following detailed description when read in connection with the accompanying drawing wherein.

DETAILED DESCRIPTION OF INVENTION

This invention provides a controlled-release tablet and a method for its preparation. The tablet of this invention achieves nearly linear (zero-order), or parabolic release kinetics for delivering water-soluble drugs over a long period of time at a nearly constant rate. The device comprises a body having a donut-like configuration with a cylindrical hole extending coaxially through the center of the body. The core material of the body comprises at least one active pharmaceutical agent and at least one hydrophilic, water-soluble, polymeric carrier. The core material is coated with a hydrophobic, water-insoluble material covering all of the core material except that which is defined by the cylindrical hole.

Figure 1:
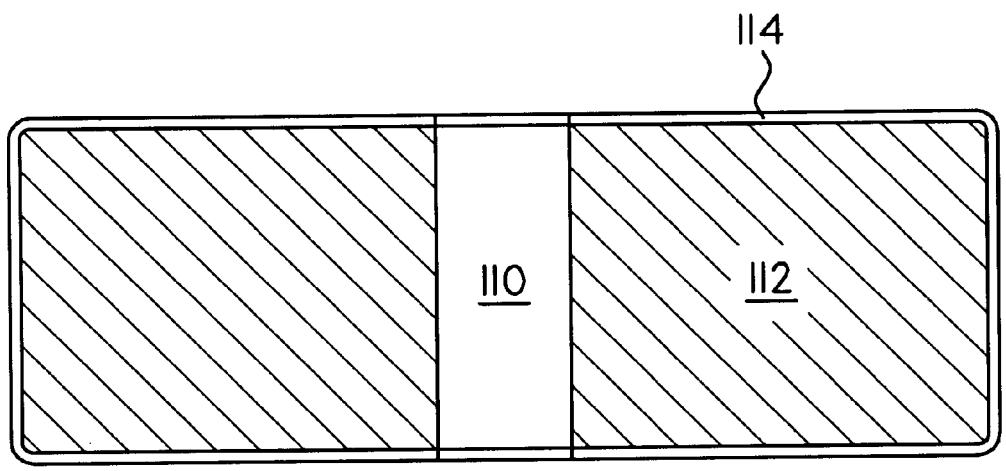
FIG. 1 is a partial section view of a device according to the present invention.

FIG. 1 is a partial section view of a device according to the present invention. Hole 110 extends through the center of the tablet. The core region 112 is comprised of an active pharmaceutical ingredient, a water soluble, hydrophilic, polymeric carrier, and, optionally, an excipient. Hydrophobic, water insoluble coating 114 is present everywhere on the outside surface of core region 112 except that surface of the core region 112 exposed to the hole 110.

Also included in the present invention is a method of preparing the device for the controlled release of an active ingredient. The method comprises the steps of blending an active pharmaceutical ingredient and a water soluble, hydrophilic, polymeric carrier to form a mix; optionally adding an excipient; compressing the mix; punching a tablet from the mix; coating the tablet in a hydrophobic, water-insoluble material; and drilling a hole in the tablet.

A second embodiment of this method includes the additional steps of drilling a first hole through the tablet before it is coated, coating the drilled tablet, and then drilling the tablet a second time with a hole larger than the first drilled hole. This method allows the tablet to be placed on a rod (through the first drilled hole) and inserted into the coating material during the coating process. After coating, the rod is removed and the second drilling is performed to insure that the inner exposed area is clear of all coating material.

The experimental results discussed below demonstrate that erosion controlled, and swelling/erosion controlled, systems can provide zero-order release dosage forms provided a constant surface area for release is maintained during drug release. Hydrophilic, water-soluble, polymeric carriers having erosion controlled or swelling/erosion controlled properties generally furnish a short release time. Despite that fact, by constricting the surface area available for release, one can extend the release time while maintaining the erosion controlled, or swelling/erosion controlled, properties.

For purposes of this invention, "erosion" of the hydrophilic material is the same physical process as "dissolution" of the hydrophilic material into the solvent. Generally, however, in the interest of clarity with respect to discussion of this invention, the hydrophilic materials will "erode" out of the tablet and the drug will "dissolve" into the solvent.

An "erosion controlled" system is one in which the most significant factor on the overall release kinetics is the rate of erosion of the carrier out of the core. Some hydrophilic materials swell before eroding, and some even swell while eroding. In these two cases, overall release kinetics will be described as being swelling/erosion controlled. That is to say, in swelling/erosion controlled cases, the most significant factor on the overall release kinetics is the rate of swelling and erosion (taken together) of the hydrophilic material as it leaves the core of the device.

In general, for a tablet of given size, drug release is governed by both the dissolution of the drug and the erosion and/or swelling of the hydrophilic, polymeric carrier. At high drug loading, there is relatively less hydrophilic, polymeric carrier present than in the case of low drug loading. Thus, in the case of a high-drug loaded tablet, erosion and/or swelling effects of the hydrophilic, polymeric carrier have less of an impact than in the case of the low-drug loaded tablet where relatively more of the hydrophilic, polymeric carrier is present. This fact can be exploited, as it is in the present invention, to develop drug-release tablets which achieve the desired drug release rates.

Water soluble, hydrophilic, polymeric carriers referenced in regard to this invention are those which dissolve completely in water at 25° C. within 24 hours. More particularly, those hydrophilic, polymeric carriers which are used herein as the hydrophilic, water-soluble component in the core material are those which, beginning as a flat, 500 mg tablet having an 11 mm diameter (and no hole), visibly completely dissolve in water at 25° C. within 24 hours of being placed in the water.

Experimental procedures and the results of experiments performed according to those procedures are discussed below. The following table displays the materials used and, in some cases, select characteristics of the material.

| Material | Particular Characteristics | Supplier |
| --- | --- | --- |
| E3* Hydroxypropylmethyl-cellulose | N/A | Dow Chemical (Ann Arbor, MI) |
| E5* Hydroxypropylmethyl-cellulose | N/A | Dow Chemical (Ann Arbor, MI) |
| E15* Hydroxypropylmethyl-cellulose | N/A | Dow Chemical (Ann Arbor, MI) |
| Polyethylene Oxide | MW = 100,000; 200,000 and 300,000 | Union Carbide Corp. (Summit, NJ) |
| Polyethylene Oxide | MW = 100,000; 200,000 and 300,000 | Aldrich Chemical (Milwaukee, WI) |
| Polyethylene Glycol | MW = 8,000 | Union Carbide Corp. (Summit, NJ) |
| Hydroxypropyl cellulose 99-EXF NF | MW = 80,000 | Hercules, Inc. (Wilmington, DE) |
| Ethylcellulose | Viscosity = 22 centipoise in 5% 80/20 tolune/ethanol solution | Aldrich Chemical (Milwaukee, WI) |
| Theophylline | N/A | Knoll AG (Ludwigshafen, Germany) |
| Magnesium Stearate | N/A | Amend Chemical (Irvington, NJ) |
| Nicardipine HCl | N/A | Sigma Chemical (St. Louis, MO) |
| Diltiazem HCl | N/A | Sigma Chemical (St. Louis, MO) |

*These are Dow Chemical names which indicate that the viscosity for each polymer in a 2% aqueous solution at 20° C. is 3, 5, and 15 centipoise, respectively.

Preparation of Tablets

First, the coated, donut-shaped tablets were prepared. A drug (or drug substitute, for purposes of experimentation and calculation of diffusion rate), a hydrophilic polymer, and magnesium stearate (1% by weight; in this experiment, the total tablet was 600 mg) were blended in a mortar and compressed to form cores using a Carver press (Carver, Inc., Wabash, Ind.) under a 6000 lb$_f$ compression force. A tablet punch was then used on the cores to produce a tablet with a flat surface having a diameter of 12.6 mm (0.496 inches). A first central hole (3/32") was bored with a high speed drill bit.

The tablets were then coated by inserting a glass rod in the hole (3/32") and dipping and rolling the cores in an ethylcellulose/dichloroethane solution (5% by weight ethylcellulose). After coating and drying, the hole size (3/32") of the coated, donut-shaped tablet was enlarged to a second size by a high speed drill bit. The final size of the hole in these experiments was either 1/8 inch or 3/16 inch. The particular hole size is indicated in the discussion below. As a general matter, hole size can range anywhere within 1/32 inch and 1/2 inch, depending on performance requirements, and one skilled in the art could readily determine the appropriate diameter.

Testing Procedure

In-vitro release of the drug component of the core material from the coated, donut-shaped tablets was carried out by dissolving each tablet and measuring diffusion of the drug into a solvent. Here, each tablet obtained pursuant to the above defined procedure was dissolved in a solvent using the USP paddle procedure on a VanKel 8000 dissolution apparatus in distilled/de-ionized water at 37° C. The stirring rate was 100 rpm, unless otherwise noted. Diltiazem HCl, theophylline, and nicardipine HCl were chosen as model drugs. The release of diltiazem HCl, theophylline, and nicardipine HCl was monitored by an HP8252A diode-array spectrophotometer at 268 nm, 244 nm, and 360 nm, respectively.

Results and Discussion

Figure 2:
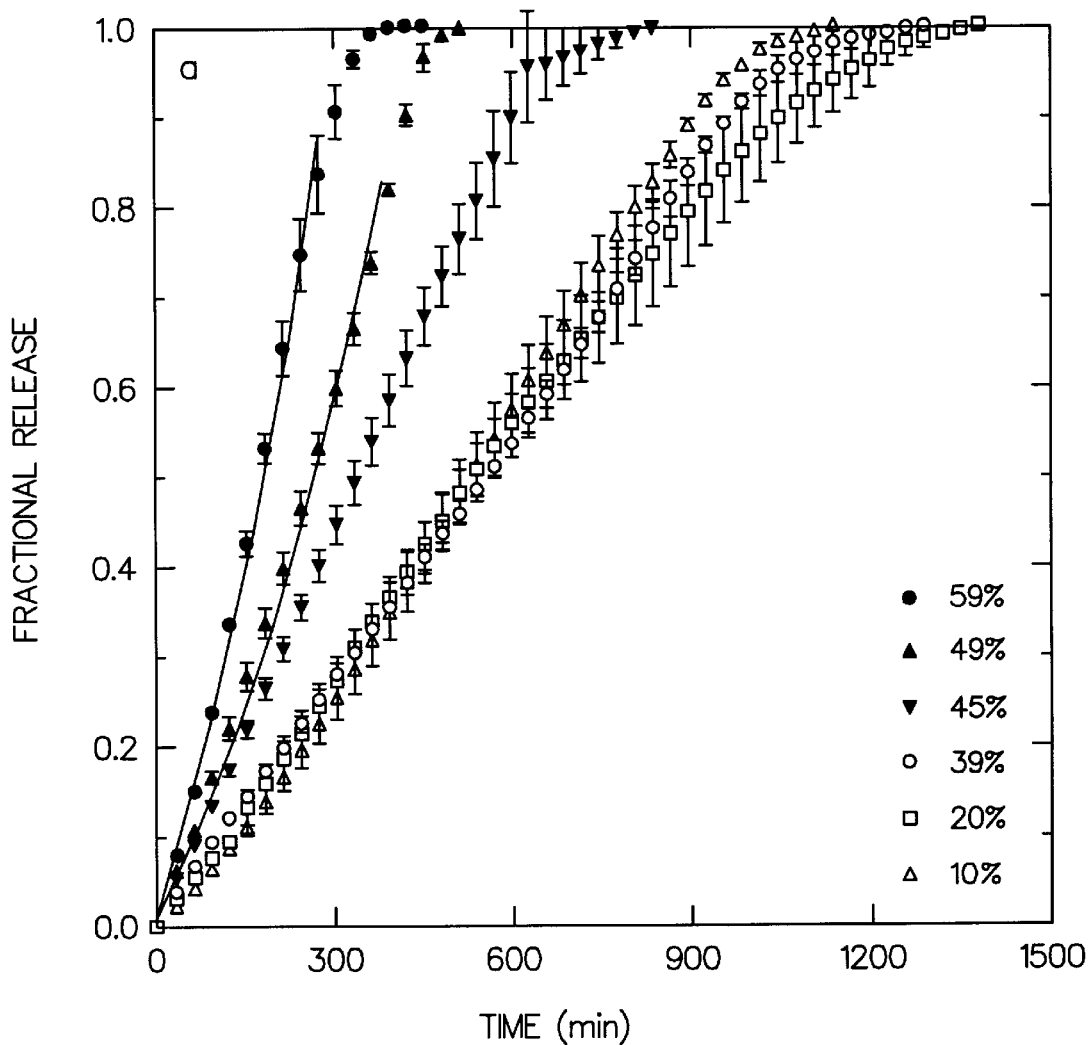
FIG. 2 is a graph illustrating fractional release of active ingredient versus time for differing active ingredient loading amounts given as percentages of overall core material.

FIG. 2 shows the effect of drug loading on the release of diltiazem HCl (solubility in water: 50%) from coated, donut-shaped tablets according to the present invention using HPMC E3 and E5 with a 3/16" hole. Coated, donut-shaped tablets (HPMC E5) with 39% by weight drug loading achieve the release of the drug at a constant rate up to 18 hours before leveling off to completion with little tailing.

"Tailing" refers to the asymptotic character of drug release as the drug is nearly completely gone from the source. In other words, the last small percentage of drug often takes a very long time to diffuse out of the matrix with respect to the first majority of drug released. Long tailing means the asymptotic value is approached slowly with respect to a short tailing release where the asymptotic value is reached relatively quickly.

As illustrated in FIG. 2, there is no significant difference in drug release kinetics of the coated, donut-shaped tablets with a drug loading of 39%, 20%, and 10% by weight. For drug loadings greater than 39% by weight, the release of the drug becomes faster as drug loading increases. It appears that release profiles become parabolic at high drug loadings (59% and 49% by weight). At high loading, drug release is governed by the dissolution of the drug or a combination of drug dissolution and polymer erosion. However, as drug loading decreases, release kinetics become linear due to a change of the controlling mechanism of drug release from the coated, donut-shaped tablets. For a drug loading level of less than 45% by weight, drug release is governed primarily by the erosion of HPMC E5. The diffusion of a freely water soluble drug (diltiazem HCl) from this matrix, however, significantly contributed to the overall release kinetics. Thus, overall, substantially linear release kinetics are observed, as shown in FIG. 2. This is especially so for drug loadings at or below 39%, out to about 1000 minutes (16 hours and 40 minutes), where some tailing begins.

Figure 3:
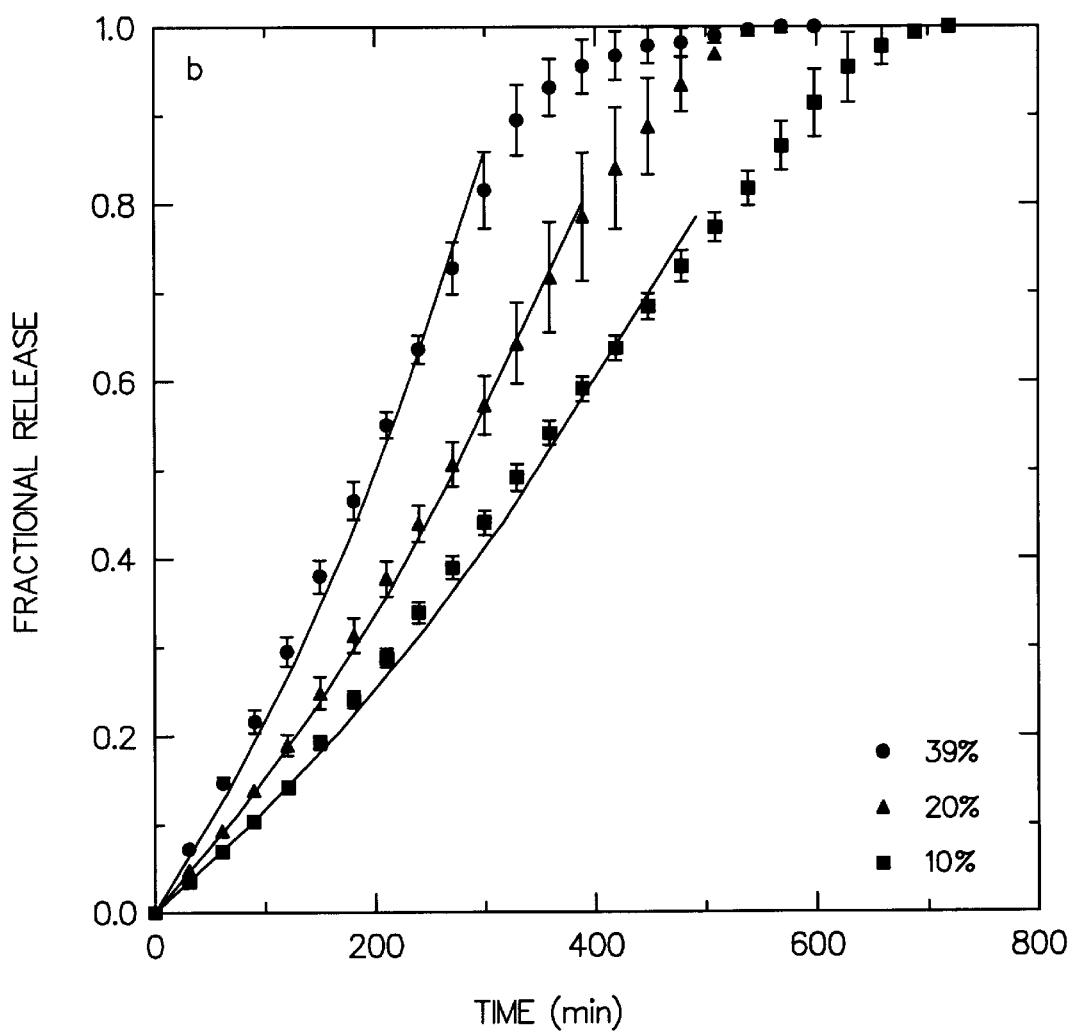
FIG. 3 is a graph illustrating fractional release of active ingredient versus time for differing active ingredient loading amounts given as percentages of overall core material.

In most cases when zero-order release kinetics from monolithic matrix systems are desired, drug diffusion in a matrix is a disadvantage. However, drug diffusion in the matrix turns into an advantage in the case of coated, donut-shaped tablets for achieving zero-order release kinetics. The release of diltiazem HCl from coated, donut-shaped tablets based on HPMC E3, as presented in FIG. 3, shows parabolic profiles for drug loadings of 10% to 39% by weight because drug release is controlled by the erosion of the carrier.

The parabolic release kinetics from coated, donut-shaped tablets can be expressed by a heterogeneous erosion mechanism if the hydrophilic, water-soluble material is highly erodible. The drug release rate at time t from a coated, donut-shaped tablet, having an outer radius $r_o$, a central hole radius a, a tablet thickness L, and an initial drug concentration $C_o$, is expressed by:

$$\frac{d M_t}{d t} = 2\pi k_e r L \quad (1)$$

where $M_t$ is the amount of drug released at time t, $k_e$ the erosion rate constant, and r the radius of the tablet at time t. The time dependent change of the tablet radius can be expressed by $$r = a + \frac{k_e}{C_o} t \quad (2)$$

Integrating equation (1) following substitution of equation (2) yields:

$$\frac{M_t}{M_\infty} = \frac{\left(\frac{a + k_e}{C_o} t\right)^2 - a^2}{r_o^2 - a^2} \quad (3)$$

where $M_\infty$ is the total amount of drug in the tablet. Release profiles of 59% and 49% by weight drug loaded coated, donut-shaped tablets (HPMC E5) shown in FIG. 2 can be represented well by equation (3) with $$\frac{k_e}{C_o}$$

of 0.082 and 0.055 cm/hr, respectively. Values for $$\frac{k_e}{C_o}$$

for HPMC E3 tablets are 0.069, 0.052, and 0.041 cm/hr for 39%, 20% and 10% by weight drug loading, respectively. The release kinetics from HPMC E3 are dependent on drug loading because the erosion of HPMC E3 is enhanced by the faster absorption of water with higher drug loading.

Figure 4:
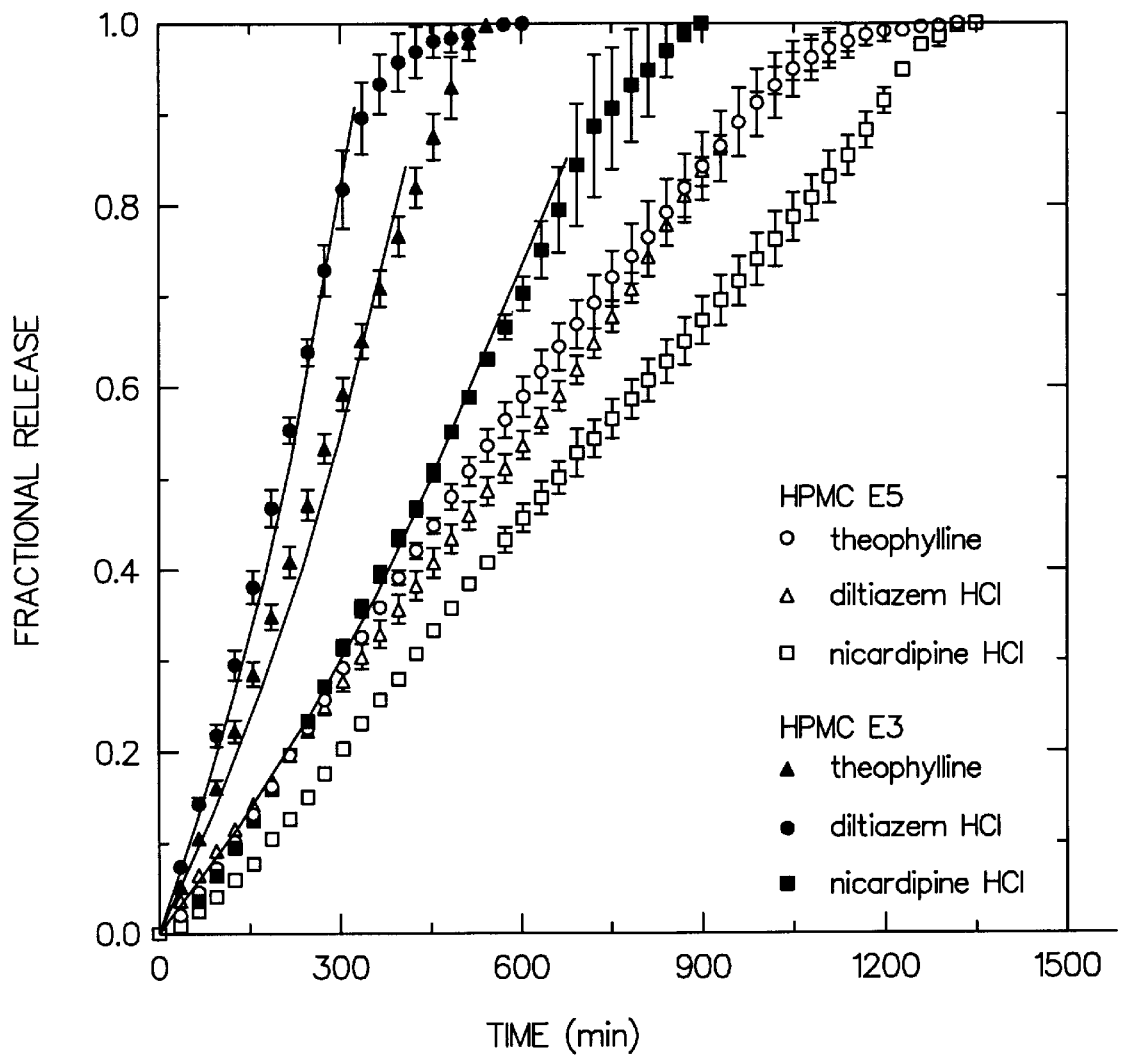
FIG. 4 is a graph illustrating fractional release of active ingredient versus time for differing active ingredients in combination with differing polymers.

The effect of drug solubility on the drug release from coated, donut-shaped tablets (HPMC E3 and E5) is shown in FIG. 4. Even though drug solubility decreases from greater than 50% (diltiazem HCl) to 1% (theophylline), drug release profiles from coated, donut-shaped tablets of HPMC E5 are essentially superimposable. This suggests that even a drug of 1% solubility provides a significantly dissolved state of drug in the matrix, resulting in a contribution of drug diffusion to the overall release kinetics. When drug solubility is 0.5% (nicardipine HCl) or less, a slight time lag at the early stage of release is observed followed by a linear release. Thus, the release of nicardipine HCl from HPMC E5 is governed largely as a function of the polymer erosion.

The release of drugs from coated, donut-shaped tablets using HPMC E3 is, however, greatly influenced by the solubility of the drugs, especially in the case where parabolic release profiles are desired. As drug solubility increases, the absorption of water becomes rapid, leading to a faster erosion of HPMC E3. When the perforated, coated tablets were fabricated with a water insoluble drug carrier (i.e. ethylcellulose) or a water soluble simple excipient (i.e. lactose), the solubility of the drugs greatly influenced the drug release from perforated, coated tablets. This is presumed to be a result of increased water presence inside the matrix with increased drug solubility.

Figure 5:
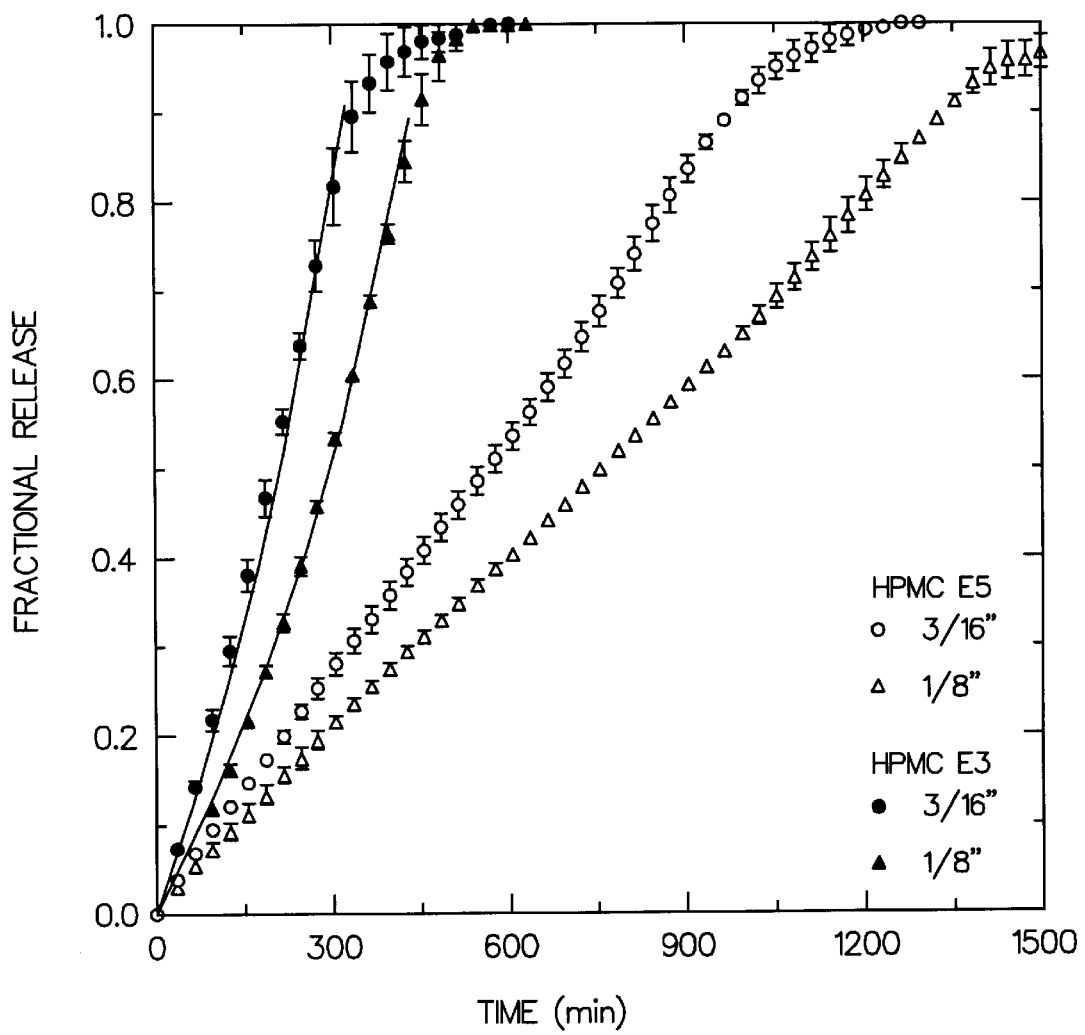
FIG. 5 is a graph illustrating fractional release of active ingredient versus time for differing polymers and for tablets having different hole sizes.

All of the coated, donut-shaped tablets mentioned above have a 3/16" hole diameter. FIG. 5 illustrates the effect of the hole diameter on the release of diltiazem HCl from coated, donut-shaped tablets. The smaller hole diameter provides a larger annular thickness, resulting in a longer release time. The release profiles from coated, donut-shaped tablets of HPMC E5 are linear through 85–90% release with no severe tailing while parabolic release profiles are maintained for coated, donut-shaped tablets of HPMC E3. One can manipulate the total drug release time by controlling the hole size and outer diameter of coated, donut-shaped tablets. It is better, however, to use a smaller hole size to fabricate coated, donut-shaped tablets because there is an increased possibility of coating the central hole surface of larger holed tablets when a mass production technology (pan and fluidization coating) is used.

Figure 6:
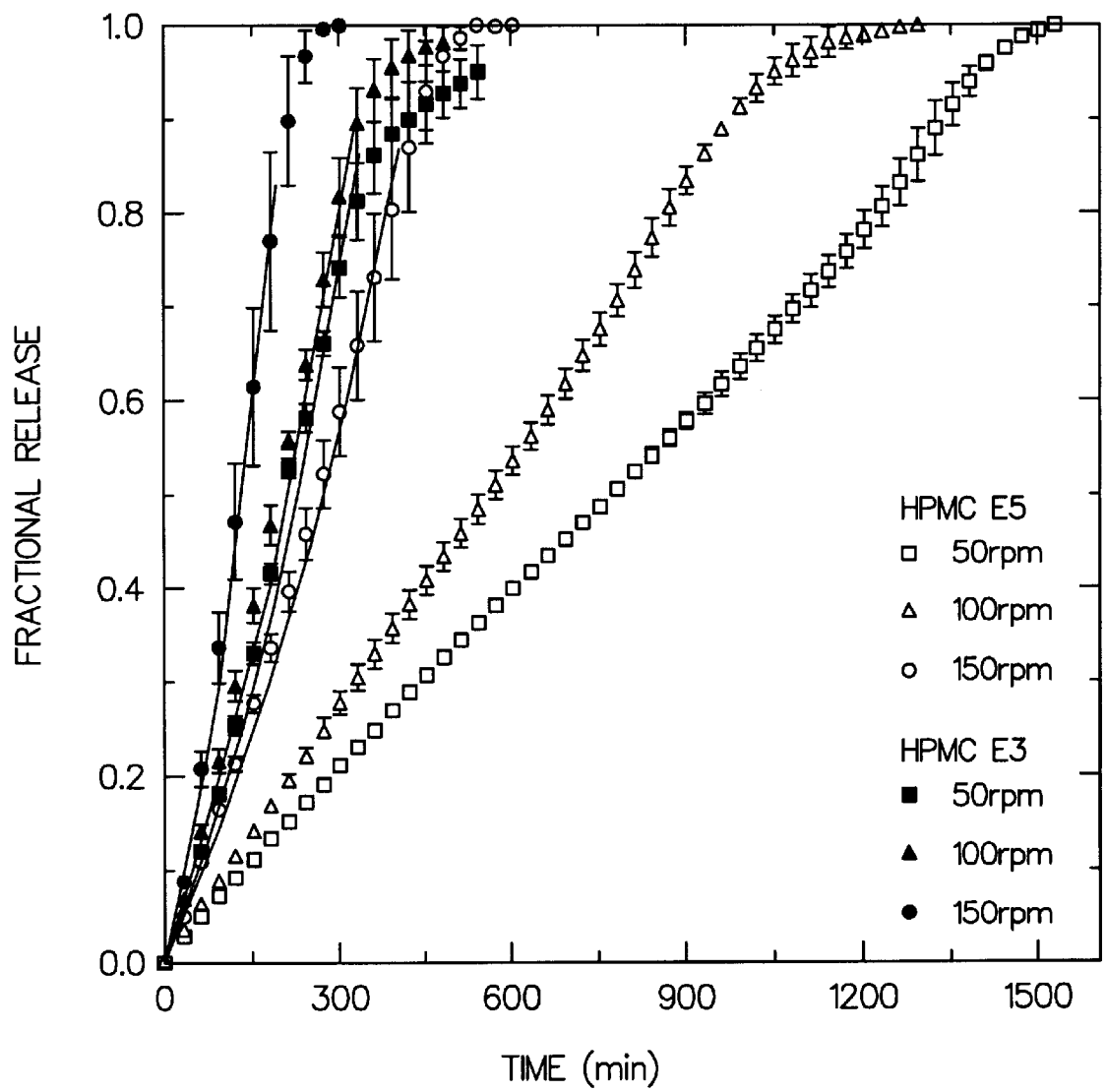
FIG. 6 is a graph illustrating fractional release of active ingredient for differing polymers and for differing mixing rates.

Another factor affecting solubility rates is agitation. Increasing the stirring rate influences the erosion of the hydrophilic, water-soluble carrier so that the release rate of drugs from the erodible matrices is facilitated. FIG. 6 displays the effect of the stirring rate on the release of diltiazem HCl from the coated, donut-shaped tablets (HPMC E3 and E5) with a 3/16" hole diameter. As the stirring rate is increased from 50 rpm to 150 rpm, the release rate of the drug increases. This suggests that the hydrodynamic condition in the central hole significantly influences the erosion of the hydrophilic, water-soluble, polymeric carrier and the diffusion of the drug. At a stirring rate of 150 rpm, the drug release profile from coated, donut-shaped tablets of HPMC E5 (39% by weight drug loading) becomes parabolic because the contribution of drug diffusion to the overall release kinetics is minimal compared to the erosion of the hydrophilic, water-soluble, polymeric carrier.

Drug release profiles from coated, donut-shaped tablets with a 3/16" hole size based on other erodible (soluble) carriers were also ascertained. Parabolic release profiles for some hydrophilic, water-soluble, polymeric carriers have been observed. One can obtain parabolic release kinetics expressed by equation (3) when erosion or swelling/erosion controlled matrix systems are used. When 39% by weight drug loaded polyethylene oxide of $M_w=300,000$ is used, the swelling of the polymer increased relative to the use of HPMC. As a result, the collapse of the hole (3/16") is encountered at about 40% release, leading to a prolonged linear release (48 hours). When drug loading was increased to 59% by weight in coated, donut-shaped tablets of polyethylene oxide, no collapse of the hole was observed because a smaller amount of polyethylene oxide was available to swell and fill the central hole.

The release of diltiazem HCl from coated, donut-shaped tablets of polyethylene oxide ($M_w=300,000$, 59% by weight drug loading) slightly deviated from parabolic release kinetics because the diffusion of the drug plays an increased role in the overall release kinetics relative to the case where HPMC was used. When HPMC E15 was used, a linear release profile was obtained with 59% by weight drug loading. When a water insoluble polymer was used as a drug carrier (i.e., ethylcellulose), a non-linear (and non-parabolic) release profile was obtained because drug diffusion in the matrix controlled the release kinetics. This illustrates that the selection of the erodible hydrophilic water-soluble, polymeric carrier will determine the release rate and total release time along with the shape of release profile (parabolic and linear) of a coated, donut-shaped tablet. In general, parabolic release profiles are obtained if $k_e/C_o$ is larger than 0.038 cm/hr.

The following table illustrates erosion rate constants of coated, donut-shaped tablets according to the present invention. Referring to equation 2, one notices that as time changes, the rate of diffusion changes very little. This, again, empirically supports the proposition that the rates are nearly zero-order.

Erosion rate constants ($k_e/C_o$) of coated donut-shaped tablets

| Polymer | Drug | Loading % | Hole Size (inch) | Stirring Rate (rpm) | $k_e/C_o$ (cm/hr) |
|---|---|---|---|---|---|
| HPMC E3 | diltiazem | 10 | 3/16 | 100 | 0.041(±1.7%) |
| | diltiazem | 20 | 3/16 | 100 | 0.051(±2.5%) |
| | diltiazem | 39 | 3/16 | 50 | 0.065(±2.1%) |
| | diltiazem | 39 | 3/16 | 100 | 0.069(±2.7%) |
| | diltiazem | 39 | 3/16 | 150 | 0.111(±5.8%) |
| | diltiazem | 39 | 1/8 | 100 | 0.050(±0.7%) |
| HPMC E5 | diltiazem | 39 | 3.16 | 150 | 0.054(±2.9%) |
| | diltiazem | 49 | 3/16 | 100 | 0.055(±2.0%) |
| | diltiazem | 59 | 3/16 | 100 | 0.082(±2.2%) |
| Polyethylene Glycol MW = 8,000 | diltiazem | 39 | 3/16 | 100 | 0.153(±3.4%) |
| Polyethylene Oxide MW = 100,000 | diltiazem | 39 | 3/16 | 100 | 0.054(±0.9%) |
| Polyethylene Oxide MW = 200,000 | diltiazem | 39 | 3/16 | 100 | 0.040(±0.8%) |
| Polyethylene Oxide MW = 300,000 | diltiazem | 59 | 3/16 | 100 | 0.025(±1.9%) |
| Hydroxypropyl Cellulose | diltiazem | 39 | 3/16 | 100 | 0.038(±1.1%) |
| HPMC E3 | theophylline | 39 | 3/16 | 100 | 0.053(±2.6%) |
| | nicardipine | 39 | 3/16 | 100 | 0.03(±1.2%) |

Figure 7:
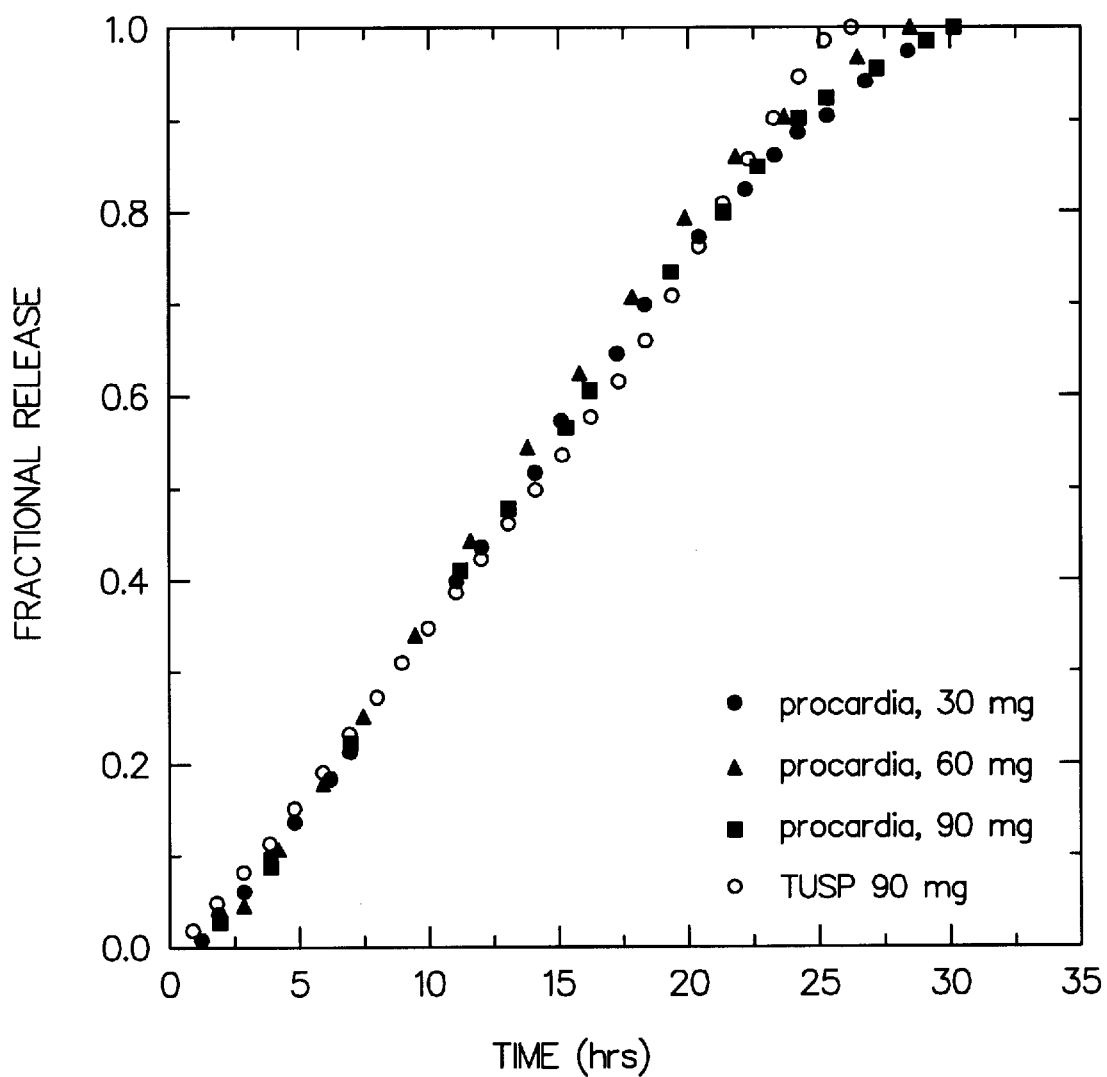
FIG. 7 is a graph illustrating fractional release of different drugs, in varying fractional amounts, versus time.
Figure 8:
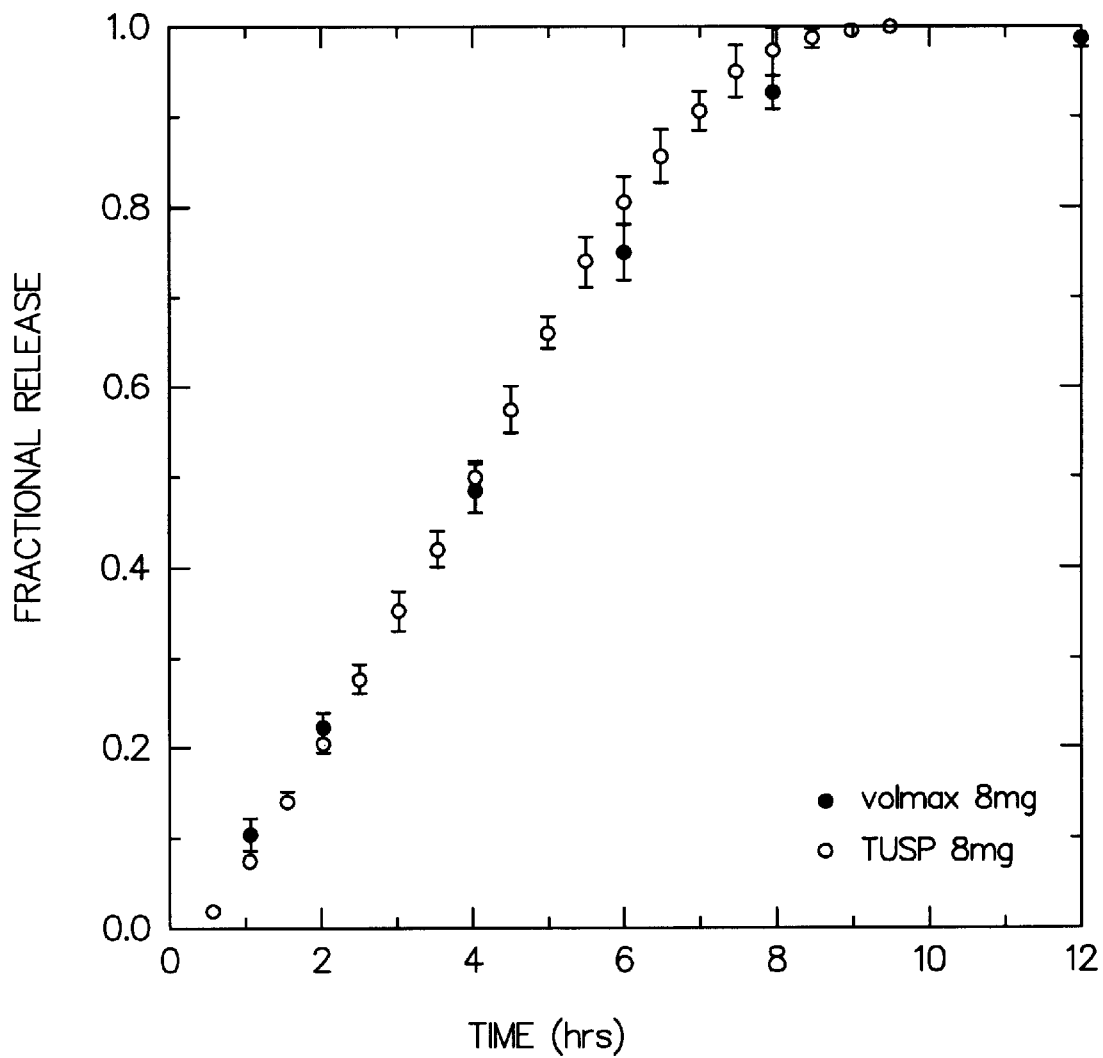
FIG. 8 is a graph illustrating fractional release of different drugs, in varying fractional amounts, versus time.

FIGS. 7 and 8 illustrate fractional release of different drugs, in varying fractional amounts, versus time. More particularly, FIG. 7 shows the fractional release of Procardia in HPMC E3 when Procardia is loaded in amounts of 30 mg, 60 mg, and 90 mg. Also shown is the fractional release over time of TUSP in HPMC E3 when TUSP is loaded to 90 mg. One can see that nearly linear release is achieved in these cases for release occurring up to 25 hours.

FIG. 8 is shows the fractional release of Volmax and TUSP loaded in HPMC E3 versus time. In FIG. 8, eight (8) mg of Volmax was loaded and 8 mg of TUSP was loaded. Here, nearly linear release occurred for about the first 8 hours.

Although most examples have focused on the use of particular polymers as the hydrophilic water-soluble carrier, other polymeric materials may be used. One example of such a polymeric, hydrophilic, water-soluble carrier is cyclodextrin, in any of its three forms ( , β, γ). One skilled in the art could readily determine other such hydrophilic, water-soluble, polymeric carriers. Several cyclodextrin derivatives, for example, could be used as the hydrophilic, water soluble, polymeric carrier material.

Although this invention has been described with reference to specific embodiments thereof, it is understood that other embodiments and variations of the invention as described and exemplified may be made by those skilled in the art without departing from the true spirit of the invention. It is intended that the appended claims be construed to include all such embodiments and variations.

What is claimed:

1. A tablet for the controlled release of a pharmaceutically active ingredient, said tablet comprising:

a donut-shaped core material with a cylindrical hole extending through the center of said core, said core comprising at least one pharmaceutically active ingredient dispersed in at least one hydrophilic, polymeric carrier which is water-soluble at body temperature, has a molecular weight from 8,000 to 300,000, and is selected from the group consisting of hydroxypropylmethylcellulose; polyethylene oxide; polyethylene glycol; hydroxypropyl cellulose; hydroxyethylcellulose; cyclodextrin; and cyclodextrin derivatives; and a coating of hydrophobic, water-insoluble material covering all of said core except the surface of said core surrounding said cylindrical hole.

2. The tablet according to claim 1 wherein said hole has a diameter in the range of 1/32 to 1/2 inches.

3. The tablet of claim 1 wherein said coating is ethylcellulose.

4. A tablet for the controlled release of a pharmaceutically active ingredient, said tablet comprising:

a core material with a hole extending through the center of said core, said core comprising at least one pharmaceutically active ingredient dispersed in at least one hydrophilic, polymeric carrier which is water-soluble at body temperature, has a molecular weight from 8,000 to 300,000, and is selected from the group consisting of hydroxypropylmethylcellulose; polyethylene oxide; polyethylene glycol; hydroxypropyl cellulose; hydroxyethylcellulose; cyclodextrin; and cyclodextrin derivatives; and a coating of hydrophobic, water-insoluble material covering all of said core except the surface of said core surrounding said hole.

5. The tablet of claim 4 wherein said coating is ethylcellulose.

6. The tablet according to claim 4 wherein said hole has a diameter in the range of 1/32 to 1/2 inches.

* * * * *